United States Patent [19]

Vora

[11] Patent Number: 4,520,214

[45] Date of Patent: May 28, 1985

[54] HIGH SELECTIVITY PROCESS FOR DEHYDROGENATION OF PARAFFINIC HYDROCARBONS

[75] Inventor: Bipin V. Vora, Elk Grove Village, Ill.

[73] Assignee: UOP Inc., Des Plaines, Ill.

[21] Appl. No.: 596,867

[22] Filed: Apr. 4, 1984

[51] Int. Cl.$^3$ .......................... C07C 5/327; C07C 5/00
[52] U.S. Cl. ..................... 585/254; 585/259; 585/262; 585/315; 585/324; 585/654; 208/255
[58] Field of Search ............... 585/254, 654, 252, 315, 585/324, 259, 262; 208/255

[56] References Cited

U.S. PATENT DOCUMENTS

| | | | |
|---|---|---|---|
| 3,234,298 | 2/1966 | van Zijll Langhout et al. | 260/677 |
| 3,472,763 | 10/1969 | Cosyns et al. | 208/255 |
| 3,484,498 | 12/1969 | Berg | 260/671 |
| 3,655,621 | 4/1972 | Kasperik et al. | 260/677 H |
| 3,662,015 | 5/1972 | Komatsu et al. | 260/677 H |
| 3,696,160 | 10/1972 | Chomyn | 260/677 H |
| 4,133,842 | 1/1979 | Anderson | 585/252 |
| 4,409,401 | 10/1983 | Murtha | 568/362 |
| 4,409,410 | 10/1983 | Cosyns et al. | 585/259 |

OTHER PUBLICATIONS

Chemical Engineering, 01-26-70, pp. 86-88, "Two Processes Team Up to Make Linear Mono-Olefins", by D. B. Broughton and R. C. Berg.

*Primary Examiner*—Delbert E. Gantz
*Assistant Examiner*—Cynthia A. Prezlock
*Attorney, Agent, or Firm*—William H. Page, II; John F. Spears, Jr.

[57] ABSTRACT

An improved process for the catalytic dehydrogenation of paraffinic hydrocarbons is disclosed. Feed paraffinic hydrocarbons are dehydrogenated to yield an olefin-containing vapor stream, which is partially condensed to produce a liquid phase process stream which contains by-product diolefins along with the intended product monoolefins. The liquid phase process stream and added hydrogen are passed through a selective hydrogenation zone in which diolefins are catalytically converted to monoolefins. This increases the quality of the product monoolefin stream. The selective hydrogenation zone is located between the vapor-liquid separator and stripper column of the dehydrogenation zone.

12 Claims, 1 Drawing Figure

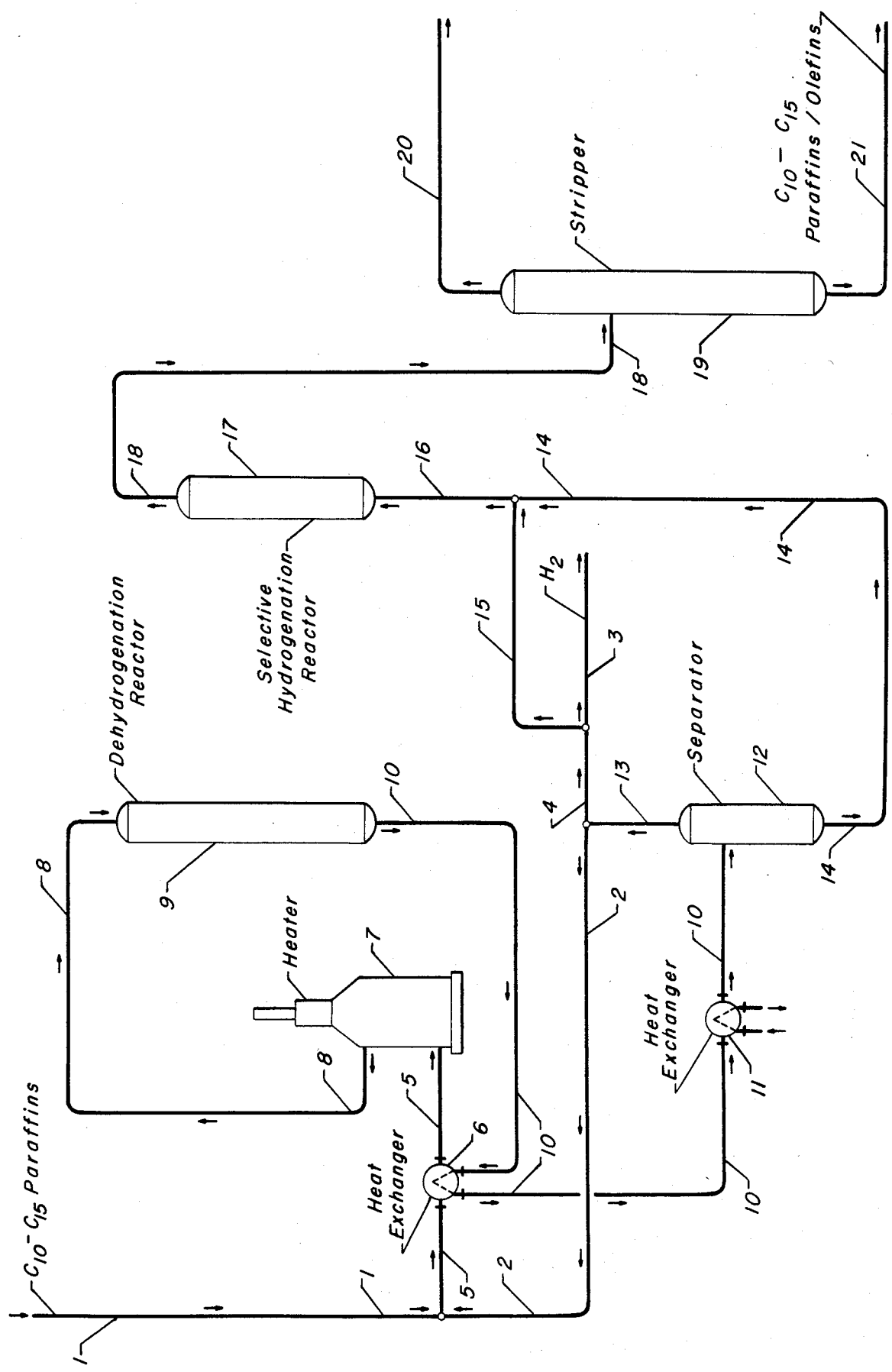

HIGH SELECTIVITY PROCESS FOR DEHYDROGENATION OF PARAFFINIC HYDROCARBONS

FIELD OF THE INVENTION

The invention relates to the broad field of hydrocarbon processing. The invention may also be broadly classified as relating to a process for the production of olefinic hydrocarbons. More specifically, the invention relates to a hydrocarbon conversion process for the selective catalytic dehydrogenation of acyclic paraffinic hydrocarbons to produce monoolefinic hydrocarbons. The invention is directly concerned with the specific method used to perform a selective hydrogenation of diolefinic hydrocarbons within the dehydrogenation zone. The selective hydrogenation converts diolefins present in the dehydrogenation reactor effluent stream to monoolefins.

INFORMATION DISCLOSURE

Processes for the dehydrogenation of acyclic hydrocarbons are well known to those skilled in the hydrocarbon conversion arts Such processes are operated commercially in petroleum refineries and petrochemical plants. A representative process flow diagram of a dehydrogenation process is provided in an article appearing at pages 86–88 of the Jan. 26, 1970 issue of *Chemical Engineering*. The process is also described in U.S. Pat. No. 3,484,498 issued to R. C. Berg. The former reference illustrates the passage of a normal paraffin charge stream into a dehydrogenation reactor, with the effluent of this zone passing through a heat exchanger in which the vapor phase reactor effluent is partially condensed. The resultant mixed phase material is passed into a separating zone in which it is separated into a hydrogen-rich recycle stream and a liquid phase process stream. The liquid phase process stream is passed through a stripping column. Hydrocarbons which remain after stripping off the light hydrocarbons are passed into a downstream facility as the net product stream of the dehydrogenation zone.

U.S. Pat. No. 3,696,160 issued to K. D. Chomyn is pertinent for its teaching that those skilled in the art of hydrocarbon processing are aware that it may be beneficial to selectively hydrogenate diolefins to monoolefins in certain hydrocarbon streams. This reference is directed to the selective conversion of propadiene and butadiene contaminants in propylene and butene charge stocks employed in alkylation processes for the production of aviation and motor fuel. In this alkylation process, a $C_3$–$C_4$ feed stream is converted to a high octane $C_7$–$C_8$ product. It is stated that a small diolefin content in the alkylation feed stream is undesirable because of increased acid consumption as a result of forming tarry acid-diolefin condensation products, which decreases the profitability of the process. The reference indicates that supported nickel and palladium catalysts are excellent hydrogenation catalysts in the diolefin conversion service, but that their tendency to deactivate in sulfur-containing feedstocks limits their utilization. The reference discloses the use of a sulfided nickel-tungsten catalyst.

U.S. Pat. No. 3,655,621 issued to A. S. Kasperik et al illustrates a process for the selective hydrogenation of $C_4$ diolefins in an alkylation feed stream employing a catalyst comprising presulfided nickel supported on a refractory base. In U.S. Pat. No. 3,234,298 issued to W. C. van Zijll Langhout et al, a process is disclosed for the selective hydrogenation of light, diene-containing cracked hydrocarbon oils. This process is employed to increase the stability of such materials as pyrolysis gasoline and kerosene obtained by severe thermal cracking operations. Such hydrogenation is desirable to reduce the gum-forming characteristics and other undesirable properties of these hydrocarbon mixtures. The process is described as being applicable to diene-containing hydrocarbons ranging from $C_3$ to $C_{18}$ in carbon number. The process employs a catalyst comprising sulfided nickel on alumina or sulfided molybdenum on alumina.

U.S. Pat. No. 3,472,763 issued to J. Cosyns et al is pertinent for its description of a selective diolefin hydrogenation catalyst which comprises nickel supported on an alumina substrate having a number of specified characteristics and for its teaching of the utility of this catalyst. Specifically, it is taught that this catalyst may be employed for the conversion of all types of conjugated diolefins to monoolefins and in particular to the conversion of aliphatic conjugated diolefins having up to 15 carbon atoms per molecule to the corresponding monoolefins. The invention is also described as being useful in the selective hydrogenation of alpha alkenyl aromatic hydrocarbons to the corresponding alkylaromatic hydrocarbons. Another application of the process is the selective hydrogenation of gasolines containing diolefins and other gum-forming hydrocarbons.

The use of catalysts which comprise palladium supported on a refractory material is described in U.S. Pat. Nos. 3,662,015 issued to Y. Komatsu et al; 4,409,401 issued to T. P. Murtha; and 4,409,410 issued to J. Cosyns et al.

BRIEF SUMMARY OF THE INVENTION

The invention provides an improved process for the production of acyclic olefinic hydrocarbons by eliminating or at least substantially reducing the concentration of diolefins in the dehydrogenation effluent stream. These improved results are obtained through the use of a selective hydrogenation reactor placed at a unique location within the overall dehydrogenation zone. The selective hydrogenation reactor is located between the product separator and the product stripper. The subject invention is therefore an integrated process rather than a separate post treatment step. This arrangement requires only a very minimal increase in the complexity and capital costs of the overall process to achieve a greatly significant improvement in operational performance.

One broad embodiment of the invention may be characterized as a process for the dehydrogenation of paraffinic hydrocarbons which comprises the steps of passing a feed stream comprising hydrogen and at least one $C_4$-plus paraffinic feed hydrocarbon through a dehydrogenation reaction zone maintained at dehydrogenation conditions and thereby producing a vapor phase dehydrogenation reactor effluent stream which comprises hydrogen, by-product light hydrocarbons having fewer carbon atoms per molecule than the feed hydrocarbon, $C_4$-plus paraffinic feed hydrocarbons, and $C_4$-plus mono- and diolefinic hydrocarbons; cooling and partially condensing the dehydrogenation reactor effluent stream and separating the dehydrogenation reactor effluent stream in a vapor-liquid separation zone into a vapor phase process stream which comprises hydrogen and a liquid phase process stream which comprises dissolved hydrogen, light hydrocarbons, C$_4$-plus paraffinic hydrocarbons, and C$_4$-plus mono- and diolefinic hydrocarbons; passing a hydrogen feed stream and the liquid phase process stream through a selective hydrogenation reaction zone which contains a selective hydrogenation catalyst and is maintained at diolefin selective hydrogenation conditions and forming a selective hydrogenation reaction zone effluent stream which comprises C$_4$-plus monoolefinic hydrocarbons and is substantially free of C$_4$-plus diolefinic hydrocarbons; and passing the selective hydrogenation reaction zone effluent stream into a stripping column operated at conditions which result in the concentration of substantially all hydrogen and light hydrocarbon present in the hydrogenation zone effluent stream into a stripping column overhead stream, and producing a stripping column bottoms stream which comprises C$_4$-plus paraffinic hydrocarbons and C$_4$-plus monoolefinic hydrocarbons and which is removed from the process as a product stream.

DESCRIPTION OF THE DRAWING

The drawing is a simplified process flow diagram of a preferred embodiment of the invention.

Referring now to the drawing, a paraffin feed stream comprising an admixture of C$_{10}$–C$_{15}$ normal paraffins enters the process through line 1. This feed stream is admixed with hydrogen from line 2 and passed into line 5. The mixture of paraffins and hydrogen flowing through line 5 is first heated in the indirect heat exchanger 6 and is then passed into a fired heater 7. The resultant vapor phase mixture of paraffins and hydrogen is passed through line 8 into a dehydrogenation reactor 9. Inside the reactor 9, the paraffins are contacted with a dehydrogenation catalyst at conditions which affect the conversion of a significant amount of the paraffins to the corresponding olefins.

There is thus produced a vapor-phase reactor effluent stream carried by line 10 which comprises a mixture of hydrogen unconverted paraffins, C$_{10}$–C$_{15}$ monoolefins, a smaller amount of C$_{10}$–C$_{15}$ diolefins, and C$_1$–C$_9$ hydrocarbons produced as undesired by-products of the dehydrogenation reaction and by thermal cracking. This reactor effluent stream is first cooled by indirect heat exchange in the feed-product heat exchanger 6 and is then further cooled in the indirect heat exchange means 11. This cooling is sufficient to condense substantially all of the C$_{10}$-plus hydrocarbons into a liquid phase process stream which separates from the remaining vapor, which is rich in hydrogen. This mixed phase stream enters the vapor-liquid separation vessel 12 wherein it is divided into a hydrogen-rich vapor phase stream removed through line 13 and a liquid phase process stream removed through line 14. The vapor phase stream is divided into a hydrogen product stream removed through lines 3 and 4 and a hydrogen recycle stream carried by line 2.

The liquid phase process stream removed from the bottom of the separator 12 contains unconverted C$_{10}$–C$_{15}$ paraffins, C$_{10}$–C$_{15}$ mono- and diolefins, lighter hydrocarbons produced as by-products, and some dissolved hydrogen. A controlled volume of hydrogen from line 15 is admixed into the liquid process stream. It is then passed through line 16 into a selective hydrogenation reactor 17. In this reactor, the liquid phase hydrocarbons and hydrogen are contacted with a catalyst under conditions which promote the selective hydrogenation of diolefins to monoolefins. The liquid phase effluent of the selective hydrogenation reactor is then passed through line 18 to a stripper column 19. In this column, the light hydrocarbons produced in the dehydrogenation reactor and heater as by-products and any remaining unconsumed hydrogen are separated from the C$_{10}$-plus hydrocarbons and concentrated into a net overhead stream removed from the process through line 20. The remainder of the hydrocarbons entering the stripper are concentrated into a net bottoms stream carried by line 21, which is removed from the process as the product stream. This stream comprises an admixture of C$_{10}$–C$_{15}$ paraffins and monoolefins and has a greatly reduced concentration of diolefins compared to the dehydrogenation reactor effluent.

DETAILED DESCRIPTION

The production of acyclic olefinic hydrocarbons is a highly useful hydrocarbon conversion process. The product olefinic hydrocarbons find utility in the production of a wide variety of useful chemicals including synthetic lubricants, detergents, polymers, alcohols, plasticizers, etc. Modern catalytic dehydrogenation processes provide a high degree of selectivity. However, they are still troubled by the production of light by-products, basically due to thermal cracking reactions and to undesired catalytic dehydrogenation side reactions. The by-products fall into two broad classes, light hydrocarbons formed by cracking reactions and diolefinic hydrocarbons having the same carbon number as the desired monoolefinic hydrocarbons. The production of diolefinic hydrocarbons is more troublesome, especially when the objective is to produce high purity monoolefinic hydrocarbons. The light by-products which result from cracking reactions can normally be readily removed from the olefin-containing product stream by a relatively easy fractional distillation step. In comparison, diolefinic hydrocarbons are normally much more difficult to remove from a product stream since their physical characteristics such as volatility are very close to those of the product monoolefins. Furthermore, the presence of diolefins in a dehydrogenation zone effluent is often undesirable because the diolefins react in downstream processes to form different compounds than the monoolefins.

It is therefore an objective of the subject invention to provide an improved process for the catalytic dehydrogenation of acyclic C$_4$-plus hydrocarbons. It is another objective of the subject invention to reduce the concentration of diolefinic hydrocarbons present in the product stream of a catalytic paraffin dehydrogenation process. It is a further objective to provide a method of selectively hydrogenating diolefins to monoolefins which has a very low capital and utilities cost.

The feed hydrocarbon charged to the subject process is an acyclic C$_4$-plus hydrocarbon. Preferably, the feed hydrocarbon is a normal paraffin. Paraffins which contain six or more carbon atoms per molecule are preferred over C$_4$ and C$_5$ paraffins. The upper limit on the carbon number of the charge stock is basically set by the volatility and processability of the charge stock in the dehydrogenation reactor. This upper limit is at about C$_{22}$ paraffins. The feed stream may be a high purity stream of a single paraffin or the feed stream may comprise a mixture of two or more paraffins having different carbon numbers. For instance, an admixture of C$_{10}$ to C$_{15}$ normal paraffins is often passed through a dehydrogenation zone to produce linear olefins which are consumed in the production of linear alkylbenzenes suitable for use in the production of biodegradable detergents.

It has now been found that the objectives set forth above can be achieved through relatively simple modification of the dehydrogenation unit. This modification performs a selective hydrogenation of diolefinic hydrocarbons produced in the dehydrogenation reactor. This selective hydrogenation converts at least a substantial amount of the diolefinic hydrocarbons to monoolefinic hydrocarbons, which are the desired product of the dehydrogenation unit. The concentration of undesired diolefinic hydrocarbons in the net effluent of the dehydrogenation section of the process is decreased. The subject process also provides a higher net yield of the desired monoolefins and a higher purity product. Perhaps most importantly, it has also been found that equipment required to perform the selective hydrogenation can be minimized by performing the hydrogenation step just downstream of the customary vapor-liquid or product separator of the dehydrogenation zone. This provides a low cost and facile method of performing the hydrogenation.

It is believed that heretofore attempts to improve the quality of an olefin-containing stream by selective hydrogenation have been in the form of separate processing operations which were not integrated into the dehydrogenation zone. That is, they appear to be described as separate operating steps which treat an olefinic feed stream charged to a selective hydrogenation process. They thus require separate process equipment such as heaters, control systems, product strippers, etc. to deliver a product stream equivalent to that provided by the subject process.

The equipment used in the process is preferably configured substantially as shown in the drawing. In this arrangement, a fresh paraffinic hydrocarbon feed stream is combined with recycled hydrogen. This forms a reactant stream which is heated by indirect heat exchange and is then passed through a bed of a suitable catalyst maintained at the proper dehydrogenation conditions of temperature, pressure, etc. The effluent of this catalyst bed or reactor effluent stream is cooled and partially condensed. Part of the uncondensed material is employed as the hydrogen-rich recycle gas stream. The remainder of the uncondensed hydrogen-rich material is the net production of hydrogen which may be used in other applications such as desulfurization. As used herein, the term "rich" is intended to indicate a molar concentration of the indicated compound or class of compounds above 50%. The separation zone also produces a liquid stream referred to herein as the liquid phase process stream. This stream is basically an admixture of dehydrogenated and undehydrogenated acyclic hydrocarbons including diolefinic hydrocarbons. This liquid phase stream will also contain some dissolved hydrogen and light hydrocarbons produced by various cracking reactions which occur at the high temperatures employed in the dehydrogenation reactor.

In the subject process, the liquid phase process stream withdrawn from this separation zone is passed into a selective hydrogenation reaction zone. This zone contains a selective hydrogenation catalyst and is maintained at conditions necessary for selective hydrogenation of diolefins to monoolefins. The placement of the selective hydrogenation zone at this point makes it very simple and therefore very economical to perform the desired selective hydrogenation. One reason for this is that the reactants are in the desired liquid phase state as they leave the separation zone. A second reason is that the temperature of the liquid phase process stream as it leaves the separation zone will normally be within the desired operating range of the selective hydrogenation reaction zone.

This location for the hydrogenation zone is also preferred since it allows the effluent of the hydrogenation zone to be stripped of hydrogen in the same stripping column normally required for the removal of light ends from the liquid phase stream condensed out of the dehydrogenation reactor effluent. This stripping column is desired in a selective hydrogenation process to ensure that hydrogen does not enter downstream processing units. It is often highly undesired to charge hydrogen to a process unit. For instance, it is highly undesirable to admit hydrogen into an HF alkylation zone, since it would be necessary to vent this hydrogen from the alkylation zone and it would therefore be necessary to treat the vented hydrogen stream for the removal of vapor phase HF. Such treatment is costly and creates waste disposal problems. A separate but less important advantage to this process flow is that it allows at least partial utilization of the hydrogen dissolved in the liquid phase process stream in the hydrogenation step. This reduces the required rate of external hydrogen addition to the hydrogenation reactor. It thereby also increases the percentage of produced hydrogen which is available in the hydrogen-rich separator gas for removal from the process as a product stream. That is, the subject process flow at least partially consumes the dissolved hydrogen in the hydrogenation reaction rather than venting the hydrogen as part of a stripper overhead vapor.

The selective hydrogenation conditions employed in the hydrogenation zone are preferably similar to that maintained in the vapor-liquid separation zone of the prior art processes. More specifically, the minimum pressure should be sufficient to maintain the reactants as liquid phase hydrocarbons. A broad range of suitable operating pressures therefore extends from about 40 to about 1000 psig, with a pressure between about 50 and 300 psig being preferred. A relatively moderate temperature between about 25° and 250° C. is preferred. More preferably, the hydrogenation zone is maintained at a temperature between about 50° and about 80° C. The liquid hourly space velocity of the reactants through the selective hydrogenation zone should be above 1.0. Preferably, it is above 5.0 and more preferably it is between 5.0 and 35 hr.$^{-1}$. The optimum set of conditions will of course vary depending on such factors as the composition of the feed stream and the activity and stability of the hydrogenation catalyst.

Another variable operating condition is the ratio of hydrogen to diolefinic hydrocarbons maintained within the selective hydrogenation zone. The amount of hydrogen required to achieve a certain conversion is believed dependent upon reactor temperature and the molecular weight of the feed hydrocarbons. Also, some catalysts, such as a palladium on alumina catalyst which was tested, require a higher hydrogen concentration to achieve the desired degree of hydrogenation. Therefore, with some catalysts, such as the palladium catalysts, it may be desired to operate with a hydrogen to diolefinic hydrocarbon mole ratio of between 2:1 and 5:1. With this catalyst, it was determined that hydrogen concentrations above this range resulted in the saturation of a significant amount of monoolefinic hydrocarbons. This of course is undesirable as it reduces the yield of the process. With the preferred feedstock and the preferred nickel sulfide catalyst, there should be less than 2.0 times the stoichiometric amount of hydrogen required for the selective hydrogenation of the diolefinic hydrocarbons which are present in the liquid phase process stream to monoolefinic hydrocarbons. Preferably, the mole ratio of hydrogen to diolefinic hydrocarbons in the material entering the selective hydrogenation zone is maintained between 1:1 and 1.8:1. In some instances, it may be desirable to operate with a less than stoichiometrically required amount of hydrogen, with mole ratios down to 0.75:1 being acceptable.

The selective hydrogenation zone preferably comprises a single fixed bed reactor containing a cylindrical bed of catalyst through which the reactants move in a vertical direction. It is preferred that the reactants flow upward through the reactor as this provides good mixing. The catalyst may be present as pellets, spheres, extrudates, irregular shaped granules, etc. The prior art suggests the use of a number of metals on selective hydrogenation catalysts including tungsten, palladium, silver, molybdenum, and nickel. Of these metals, it is preferred that the active catalytic metal component present in the hydrogenation catalyst is either nickel or palladium, with nickel being especially preferred. When non-noble metals are employed, the catalyst should have a high concentration or loading of the active metal, with the metal component preferably comprising over 10 wt. % of the catalytic composite. More preferably, over 20 wt. % of the catalytic composite is metallic. It is very highly preferred that the selective hydrogenation catalyst also comprises a sulfur component. The preferred catalyst may therefore be described as a sulfided high nickel catalyst. The preparation of catalysts of this nature is described in U.S. Pat. No. 3,919,341. The preferred selective hydrogenation catalyst has a lower sulfur concentration than the catalyst described in this reference, with sulfur levels between about 0.1 and 0.4 wt. % being preferred. The basic function of the sulfur component is believed to be the attenuation of the hydrogenation activity of the nickel. It is known in the art that carbon monoxide may be passed into a selective hydrogenation reactor for the purpose of moderating or attenuating the hydrogenation reaction. The use of carbon monoxide and other such moderators though not necessary may be employed.

The selective hydrogenation catalyst also comprises a support or carrier material which should be relatively inert and refractory to the conditions employed within the process. The support can be formed from a variety of porous materials including various clays, diatomaceous earth, aluminas, ceramics, attapulgus clay, and other synthetically prepared or naturally occurring silicates, kaolin, kieselguhr, titania, alumina, crystalline aluminosilicates, and admixtures of two or more of these materials. The especially preferred carrier material is an alumina. Of the aluminas, gamma-alumina is preferred. The carrier material or support may have an apparent bulk density of about 0.3 to about 0.8 g/cc, a surface area of about 50 to about 550 m$^2$/g, and a pore volume of between about 0.1 to about 1.0 ml/g.

The effluent of the selective hydrogenation zone is a liquid phase stream similar in nature to the liquid phase process stream removed from the separator but having a reduced concentration of diolefinic hydrocarbons and a corresponding increase in the concentration of monoolefinic hydrocarbons. This effluent stream is passed into a stripping column designed and operated to remove overhead all compounds which are more volatile than the lightest hydrocarbon which it is desired to have present in the net effluent stream of the dehydrogenation process. These lighter materials will be concentrated into a net overhead stream which will comprise an admixture of hydrogen and light hydrocarbons. The purpose of the stripping operation is to prevent the entrance of volatile light materials into downstream processing zones where they would present certain operational problems. For example, the passage of light monoolefins into an alkylation zone would lead to the production of an increased amount of undesired side products through alkylation and polymerization reactions. The stripping column also serves to eliminate the light hydrocarbons from any recycle stream which returns paraffinic hydrocarbons to the dehyrogenation zone from the downstream processing units.

The composition of the dehydrogenation catalyst is not believed to materially affect the operation of the subject process provided this catalyst meets commercial standards for activity, stability, and selectivity. Dehydrogenation catalysts are described in U.S. Pat. Nos. 3,274,287; 3,315,007; 3,315,008; 3,745,112; and 4,430,517. These catalysts comprise a platinum group component supported on a porous carrier material. The preferred carrier material is a refractory inorganic oxide such as gamma-alumina. The preferred dehydrogenation catalysts contain on an elemental basis 0.01 to 2 wt. % platinum group component and about 0.1 to 5 wt. % of an alkali or alkaline earth metal. Preferably, there is present 0.05 to 1 wt. % platinum group component and about 0.25 to 3.5 wt. % of the alkali or alkaline earth component. The platinum group component may be chosen from the group consisting of platinum, palladium, rhodium, ruthenium, osmium, and iridium, but platinum is highly preferred. The alkali or alkaline earth component may be selected from the group consisting of the alkali metals—cesium, rubidium, potassium, sodium, and lithium; and the alkaline earth metals—calcium, strontium, barium, and magnesium. This component is preferably either lithium or potassium, with lithium being especially preferred. Another example of a suitable dehydrogenation catalyst is a catalyst which in addition to the previously described platinum and alkali or alkaline earth metal components contains a tin component. This catalytic composite would contain from about 0.1 to about 1 wt. % tin. Yet another catalytic composite which should be highly suited for use in the subject process comprises an indium component in addition to the platinum, tin, and alkali or alkaline earth components. The indium component may be present on an elemental basis equal to about 0.1 to about 1 wt. % of the final composite. It is also known in the art that some catalytic composites of this nature may benefit from the presence of a small amount of a halogen component, with chlorine being the normally preferred halogen. Typical halogen concentrations in the final catalytic composite range from about 0.1 to about 1.5 wt. %. A halogen component is not desired in all situations. These catalytic composites are known to those skilled in the art and are described in the available references.

A preferred embodiment of the invention may accordingly be characterized as a process for the dehydrogenation of paraffinic hydrocarbons which comprises the steps of passing hydrogen and a paraffin feed stream which comprises at least one $C_{10}$-plus linear paraffinic hydrocarbon through a catalytic dehydrogenation reaction zone and forming a vapor phase dehydrogenation reaction zone effluent stream which comprises a mixture of hydrogen, $C_8$-minus dehydrogenation reaction by-product hydrocarbons, $C_{10}$-plus mono- and diolefinic linear hydrocarbons, and $C_{10}$-plus linear paraffins; separating hydrogen from the dehydrogenation reaction zone effluent stream by partially condensing the dehydrogenation reaction zone effluent stream and separating the resultant two-phase admixture in a vapor-liquid separation zone and forming a vapor phase stream which is rich in hydrogen and a liquid phase process stream comprising $C_8$-minus by-product hydrocarbons, $C_{10}$-plus linear paraffins, dissolved hydrogen, and mono- and diolefinic $C_{10}$-plus linear hydrocarbons; passing a hydrogen feed stream and the liquid phase process stream through a selective hydrogenation zone maintained at diolefin selective hydrogenation conditions and in which the liquid phase process stream is contacted with a solid selective hydrogenation catalyst and thereby forming a hydrogenation zone effluent stream which contains less than 0.4 mole percent $C_{10}$-plus diolefinic hydrocarbons; removing substantially all dissolved hydrogen and $C_8$-minus hydrocarbons from the hydrogenation zone effluent stream by passing the hydrogenation zone effluent stream into a light ends stripping column, and producing a stripping column bottoms stream which comprises a mixture of $C_{10}$-plus monoolefinic linear hydrocarbons and $C_{10}$-plus linear paraffins and which is removed from the process as a net product stream.

The net product of the process, the bottoms stream of the stripping column, can be passed into a number of downstream processing units or it can be withdrawn as a finished product. For instance, the product stream may be passed into alkylation zones wherein the olefinic hydrocarbons can be reacted with aromatic hydrocarbons or into esterification zones as in the production of plasticizers. The product stream may also be passed into an oligomerization zone or a hydration zone. Another possibility is that the net process effluent stream may be charged to a separation zone which separates the monoolefins from the unconverted paraffins. This separation could be performed by fractional distillation on a single carbon number effluent stream but would be quite a difficult and expensive fractionation. Sorptive-type separations which employ selective solid adsorbents, known in the art, are preferred for this type of separation. A broad carbon number range olefin-paraffin mixture can be charged to such a process and efficiently separated into a high purity olefin stream and a paraffin stream. The paraffin stream may then be recycled to the dehydrogenation zone.

I claim as my invention

1. In a process for the dehydrogenation of $C_4$-plus paraffinic hydrocarbons to monoolefinic hydrocarbons with a minimum presence of diolefinic hydrocarbons comprising the steps of:
   (a) passing said $C_4$-plus paraffinic hydrocarbons and hydrogen as a feed stream through a dehydrogenation reaction zone maintained at dehydrogenation conditions to produce a vapor phase dehydrogenation reaction zone effluent stream comprising:
      (i) hydrogen,
      (ii) by-product light hydrocarbons having fewer than four carbon atoms per molecule,
      (iii) undehydrogenated $C_4$-plus paraffinic hydrocarbons,
      (iv) $C_4$-plus monoolefinic hydrocarbons, and
      (v) $C_4$-plus diolefinic hydrocarbons;
   (b) cooling said dehydrogenation reaction zone effluent stream to partially condense said dehydrogenation reaction zone effluent stream to a vapor-liquid phase stream;
   (c) separating said cooled vapor-liquid phase dehydrogenation reaction zone effluent in a vapor-liquid separation zone maintained at vapor-liquid separation conditions into a separation zone overhead vapor stream comprising hydrogen and a separation zone bottoms liquid stream comprising:
      (i) dissolved hydrogen,
      (ii) by-product light hydrocarbons having fewer than four carbon atoms,
      (iii) $C_4$-plus paraffinic hydrocarbons,
      (iv) $C_4$-plus monoolefinic hydrocarbons, and
      (v) $C_4$-plus diolefinic hydrocarbons;
   the improvement which comprises passing said separation zone bottoms liquid stream and a controlled amount of a hydrogen feed stream to a selective hydrogenation reaction zone located downstream of said vapor-liquid separation zone and upstream of a stripping zone as hereinafter defined in step (d), said hydrogenation zone containing a selective hydrogenation catalyst and maintained at selective diolefin hydrogenation conversion conditions, said amount of hydrogen selected to be effective to selectively convert said diolefinic hydrocarbons to monoolefinic hydrocarbons and to produce a hydrogenation reaction zone effluent stream substantially free of $C_4$-plus diolefinic hydrocarbons; and
   (d) stripping said hydrogenation reaction zone effluent stream in a stripping zone maintained at stripping conditions effective to result in the production of a stripping zone overhead stream containing substantially all hydrogen and light hydrocarbons present in said hydrogenation zone effluent and a stripping zone bottoms stream substantially free of diolefins and containing $C_4$-plus monoolefinic hydrocarbons as the product stream of said process.

2. The process of claim 1 further characterized in that the selective hydrogenation conditions include the presence of less than 2.0 times the stoichiometrically required amount of hydrogen for the selective hydrogenation of the diolefinic hydrocarbons present in the liquid phase process stream to monoolefinic hydrocarbons.

3. The process of claim 2 further characterized in that the mole ratio of added hydrogen to diolefinic hydrocarbons in the liquid bottoms stream of the vapor-liquid separation zone passed to said hydrogenation reaction zone is maintained between 1.0:1.0 and 1.8:1.0.

4. The process of claim 3 further characterized in that the selective diolefin hydrogenation catalyst comprises nickel and sulfur and an inorganic refractory support material.

5. The process of claim 2 further characterized in that the selective diolefin hydrogenation catalyst comprises palladium and a refractory inorganic support material.

6. In a process for the dehydrogenation of $C_{10}$-plus linear paraffinic hydrocarbons to $C_{10}$-plus linear monoolefinic hydrocarbons containing less than 0.4 mole percent $C_{10}$-plus linear diolefinic hydrocarbons comprising the steps of:
   (a) passing said $C_{10}$-plus paraffinic hydrocarbons and hydrogen as a feed stream through a dehydrogenation reaction zone maintained at dehydrogenation conditions to produce a vapor phase dehydrogenation reaction zone effluent stream comprising:

(i) hydrogen,
(ii) $C_8$-minus linear dehydrogenation by-product hydrocarbons,
(iii) $C_{10}$-plus linear undehydrogenated paraffinic hydrocarbons,
(iv) $C_{10}$-plus linear monoolefinic hydrocarbons, and
(v) $C_{10}$-plus linear diolefinic hydrocarbons;

(b) cooling said dehydrogenation reaction zone effluent stream to partially condense said dehydrogenation effluent stream to a vapor-liquid phase stream;

(c) separating said cooled vapor-liquid phase dehydrogenation reaction zone effluent in a vapor-liquid separation zone maintained at separation conditions into a separation zone overhead vapor stream comprising hydrogen and a separation zone bottoms liquid stream comprising:
(i) dissolved hydrogen,
(ii) $C_8$-minus linear dehydrogenation by-product hydrocarbons,
(iii) $C_{10}$-plus linear paraffinic hydrocarbons,
(iv) $C_{10}$-plus linear monoolefinic hydrocarbons, and
(v) $C_{10}$-plus linear diolefinic hydrocarbons;

the improvement which comprises: passing said separation zone bottoms liquid stream and a controlled amount of a hydrogen feed stream to a selective hydrogenation reaction zone located downstream of said vapor-liquid separation zone and upstream of a stripping zone as hereafter defined in step (d), said hydrogenation zone containing a selective hydrogenation catalyst and maintained at selective diolefin hydrogenation conversion conditions, said amount of hydrogen selected to be effective to selectively convert said $C_{10}$-plus linear diolefinic hydrocarbons to $C_{10}$-plus monoolefinic hydrocarbons to produce a hydrogenation reaction zone effluent having less than 0.4 mole percent $C_{10}$-plus linear diolefinic hydrocarbons; and (d) stripping said hydrogenation reaction zone effluent in a stripping zone maintained at stripping conditions effective to result in the production of a stripping zone overhead stream containing substantially all hydrogen and $C_8$-minus by-product hydrocarbons present in said reaction zone effluent and a stripping zone bottoms stream comprising less than 0.4 mole percent diolefinic hydrocarbon and a mixture of $C_{10}$-plus linear paraffinic hydrocarbons and $C_{10}$-plus linear monoolefinic hydrocarbons as the product stream of said process.

7. The process of claim 6 further characterized in that the paraffinic hydrocarbon comprises a $C_{15}$ to $C_{20}$ paraffin.

8. The process of claim 6 further characterized in that the paraffinic hydrocarbons comprise a mixture of $C_{10}$ to $C_{15}$ linear paraffinic hydrocarbons.

9. The process of claim 6 further characterized in that the hydrogen feed system added to said hydrogenation zone comprises a portion of the separation zone overhead vapor stream removed from the vapor-liquid separation zone.

10. The process of claim 9 further characterized in that the hydrogenation catalyst comprises nickel, sulfur, and a refractory inorganic support.

11. The process of claim 10 further characterized in the mole ratio of added hydrogen to $C_{10}$-plus linear diolefinic hydrocarbons in the bottoms liquid stream derived from the separation zone is between 1.0:1.0 and 1.8:1.0.

12. The process of claim 9 further characterized in that the hydrogenation catalyst comprises palladium and a refractory inorganic support.

* * * * *